United States Patent [19]
Colin et al.

[11] Patent Number: 5,902,746
[45] Date of Patent: May 11, 1999

[54] ASSEMBLY FOR TREATING A SAMPLE IN A LIQUID MEDIUM, IN PARTICULAR A BIOLOGICAL MATERIAL

[75] Inventors: Bruno Colin, Marcy l'Etoile; Bernard Mandrand, Villeurbanne; Pierre Imbaud, Pommiers, all of France

[73] Assignee: Bio Merieux, Marcy L'Etoile, France

[21] Appl. No.: 08/849,515

[22] PCT Filed: Oct. 18, 1996

[86] PCT No.: PCT/FR96/01635

§ 371 Date: Jun. 9, 1997

§ 102(e) Date: Jun. 9, 1997

[87] PCT Pub. No.: WO97/15815

PCT Pub. Date: May 1, 1997

[30] Foreign Application Priority Data

Oct. 23, 1995 [FR] France .................................. 95 12669

[51] Int. Cl.$^6$ .................................................. C12M 1/42
[52] U.S. Cl. .................................... 435/306.1; 435/286.5; 435/287.2; 435/288.6; 422/68.1; 422/70; 422/101
[58] Field of Search .............................. 435/306.1, 288.6, 435/287.2, 286.1, 286.5, 288.5; 422/68.1, 70, 99, 100, 101; 210/198.2; 436/174, 177, 178; 219/427, 438, 441; 392/478

[56] References Cited

U.S. PATENT DOCUMENTS 3,615,235  10/1971  Hrdina .
4,233,494  11/1980  Pawlik et al. .
5,252,303  10/1993  Goof .
5,330,914   7/1994  Uhlen et al. .
5,346,999   9/1994  Cathcart et al. .

FOREIGN PATENT DOCUMENTS 2422884  11/1979  France .
90/12350 10/1990  WIPO .

OTHER PUBLICATIONS

C. D. Bevan et al., "Freeze–Thaw Flow Management: A NovelConcept For High–Performance Liquid Chromatography, Capillary Electrophoresis, Electrochromatography and Associated Techniques",, Journal of Chromatography A, vol. 697, No. ½, 21 Apr. 21, 1995.

*Primary Examiner*—William H. Beisner
*Attorney, Agent, or Firm*—Oliff & Berridge PLC

[57] ABSTRACT

An assembly for treating a sample in a liquid medium, in particular a biological material, includes an essentially static permanently active module, closed off by a chamber from the outside. The assembly includes a disposable outer container holding the sample to be treated, for example an inoculum of a cell culture. The disposable outer container can be connected to the main outlet of a treatment circuit. Another disposable outer container is provided for analyzing the nucleic fraction obtained in the treatment circuit. This container can be connected to the main outlet of the treatment circuit and comprises various reagents and means for analyzing the nucleic fraction. Constituents of the assembly can act as a heat source when connected to an electrical current.

12 Claims, 1 Drawing Sheet

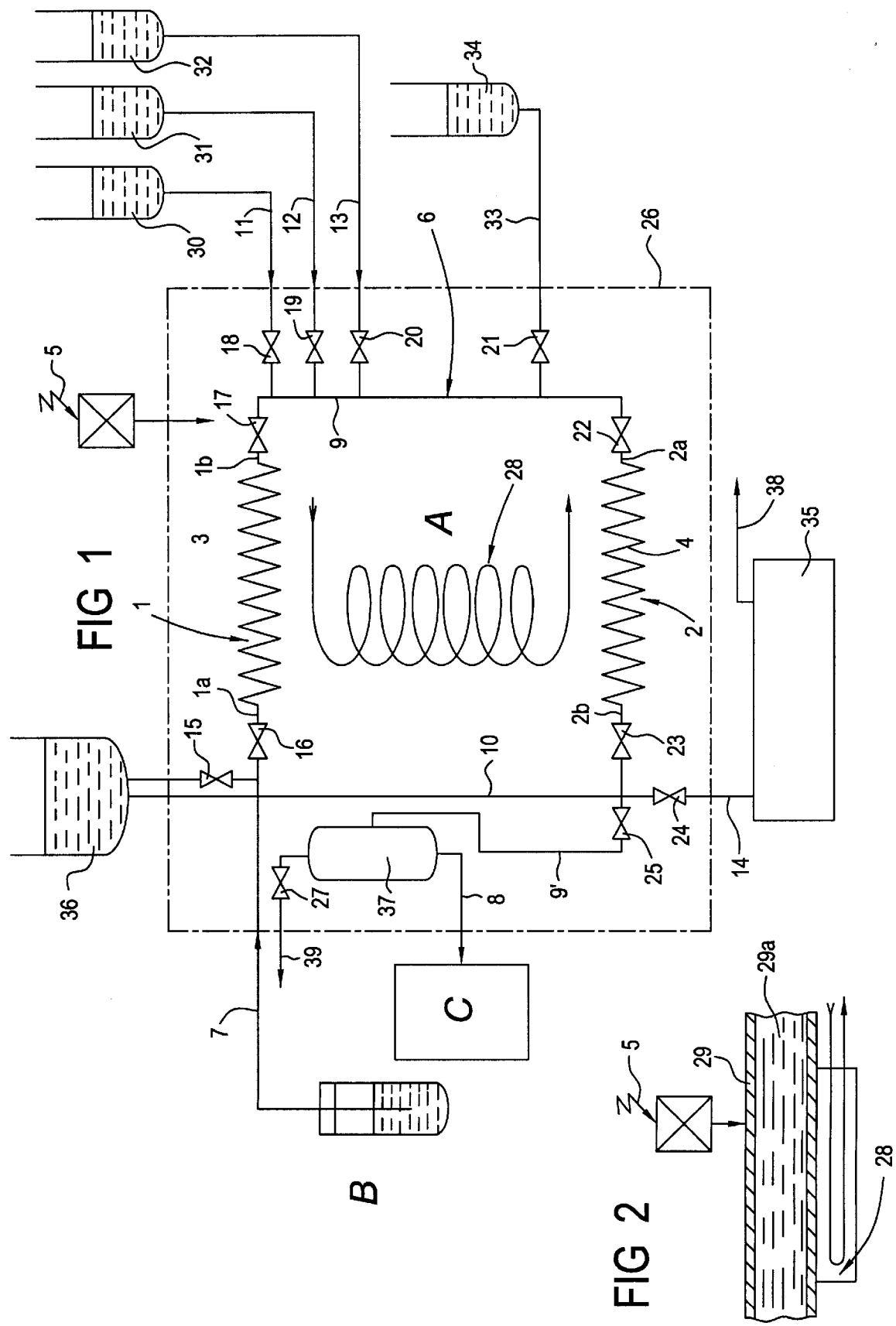

ASSEMBLY FOR TREATING A SAMPLE IN A LIQUID MEDIUM, IN PARTICULAR A BIOLOGICAL MATERIAL

BACKGROUND OF THE INVENTION

1. Field of the Invention

The present invention relates in general to the treatment of a sample in a liquid medium, in particular an aqueous medium, to release and separate a predetermined fraction of interest in said sample. In particular, but solely by way of nonlimiting example, the invention relates to the treatment of a biological material, for example a cellular material, to release and separate a constituent or predetermined fraction, of subcellular or intracellular nature, of the sample that is treated, for example a nucleic or proteinic fraction. By way of introduction to the present invention, and in order to explain it, it will hereafter be described and defined with reference to the analysis, detection, concentration or separation of a nucleic fraction in a biological sample, for example a cellular material comprising said intended nucleic fraction, in order to identify it and/or quantify it.

2. Technical Background

The subject of the present invention is an assembly for treating a sample, said assembly being sterilizable and making it possible to avoid, on the one hand any contamination of the constituent or the predetermined fraction to be analyzed, due to the prior treatment of a different sample, and on the other hand any contamination by various external sources which may, in particular, subsequently vitiate the analysis.

As regards the treatment of nucleic fractions or constituents, an object of this type is particularly important, it being known in practice that many analyses of nucleic material are interfered with or vitiated, when using the same analysis equipment, on the one hand by remnants or residues of the sample treated beforehand, and on the other hand by the existence of nucleic "pollutants" in the immediate vicinity of the analysis equipment. The analysis of nucleic fractions or constituents consequently imposes constraints, in particular operation under particularly stringent conditions, in order to avoid any parasitic contamination of the constituent or fraction to be analyzed.

SUMMARY OF THE INVENTION

The invention makes it possible to overcome these drawbacks. A treatment assembly according to the invention comprises, on the one hand an essentially static, permanent active module, closed off from the outside and combining, in a treatment circuit, in series between a main inlet for the sample to be treated and a main outlet for the predetermined fraction or constituent of the same sample:

a first chamber for dissociating the sample which is treated, in particular for lysis of the biological material, in order to release the predetermined and intended fraction or constituent, said chamber comprising a first duct element a second chamber for separating this predetermined fraction, comprising a second duct element various ducts for connection between the various elements or components of the treatment circuit various secondary inlets and/or secondary outlets for various liquid or gaseous treatment agents, and/or liquid or gaseous effluents, respectively and valves for controlling the liquid or gaseous fluids circulating in the circuit all the components of the circuit, including the first and second duct elements, being made from a mechanically strong material, in particular a metallic material, capable of dissipating heat by ohmic effect, in order to constitute a heat source directly in their body and an electrical source connected to said components, including the first and second duct elements, to pass through them, in controlled fashion, an electrical current generating a heat source directly in their body, the whole being designed for full internal incineration of the circuit, simply by passing an electrical current through the constituent materials of said circuit, and, on the other hand, a disposable outer container, for the sample to be analyzed, which can be connected to the main inlet of the treatment circuit, and a disposable outer container for analysis of the predetermined and intended fraction or constituent, in particular a card which can be connected to the main outlet of the treatment circuit, this card comprising various reagents and means for analyzing the predetermined fraction; optionally, the disposable outer container and the disposable outer card are combined as a single component or device, itself disposable.

Preferably, at least several control valves of the treatment circuit are each a valve referred to as a static valve involving freezing of the liquid of the sample, and/or any other liquid agent circulating in the treatment circuit. Each valve comprises to this end a duct element designed to receive the liud medium in its passage cross section, the wall of which is thermally conductive, and a heat sink arranged in thermal contact, in particular in heat exchange, with said duct element, the temperature and cooling power of which are tailored to the freezing of the liquid medium in said passage cross section. The duct element is dimensioned, in relation with the heat sinks and the heat source generated by passing an electrical current through it, to change rapidly, for example within an elementary time of less than 10 seconds, from a cold state, in which the liquid medium can, by freezing, seal the passage through the duct element, including against relatively high pressures, for example at least equal to 50 bar, in particular 150 bar, to a hot state in which the liquid medium is liquified, freeing said passage.

The invention thus provides a treatment assembly or system which can be automated, and implemented under conditions and in an environment which are less stringent than those usually encountered before the analysis of "sensitive" samples or materials, that is to say ones which can be contaminated or contaminate their close environment, for example the analysis operator.

BRIEF DESCRIPTION OF THE DRAWINGS

The present invention is now described with reference to the treatment of a biological sample, for the subsequent analysis of a nucleic fraction of a cellular material, with reference to the appended drawing, in which:

FIG. 1 schematically represents an analysis assembly according to the invention

FIG. 2 schematically represents a static freezing valve belongling to the analysis assembly represented in FIG. 1.

DESCRIPTION OF PREFERRED EMBODIMENTS

A treatment assembly according to the invention includes three parts, namely:

an essentially static pemanently active module A, closed off by a chamber 26 from the outside, incorporating a treatment circuit 6 described below a disposable outer container B for the sample to be treated, for enample an inoculum of a call culture; this container can be connected to the main inlet 7 of the treatment circuit 6 and another disposable outer container C, for analyzing the nucleic fraction obtained in the treatment circuit 6, which can be connected to the main outlet of the treatment circuit; in a manner which is traditional and is not described below, this container comprises various reagents and means for analyzing the nucleic fraction, for example for amplifying and/or detecting a particular nucleic fragment.

Between the main inlet 7 and the main outlet 8, the treatment circuit 6 combines:

a first duct 3, formimg a first chamber 1 for dissociating or lyzing the biological material which is treated, in this case the cell culture which is analyzed a second duct 4, forming a second chamber 2 for separating the nucleic fraction to be analyzed various connecting ducts, including one 9 between the first duct 3 and the second duct 4, and another 10 between the second duct 2 and the main duct 8 various secondary inlets 11 to 13 and/or secondary outlets 14, 39 for various liquid and/or gaseous treatment agents, and/or liquid or gaseous effluents, respectively valves 15 to 25 and 27 for controlling the liquid or gas flows circulating in the treatment circuit; the control valves 15, 16, 17, 18, 21, 22, 23, 24 and 25 are preferably so-called static freezing valves, as described below; the valve 27 is either a mechanical or traditional valve or a static freezing valve; in the latter case, it is necessary to provide liguid feed means, not represented in the appended FIG. 1.

All the components of the treatment circuit 6, including the first 3 and second 4 duct elements of the first 1 and second chambers 2, respectively, are made from a mechanically strong material, in particular a metallic material, which can dissipate heat by ohmic effect, to constitute a heat source directly in their body. To this end, an electrical source, schematically represented by the numerical reference 5, is connected to all these components, including the first and second duct elements 3 and 4 of the first 1 and second 2 chambers, respectively, to pass through them, in controlled fashion, an electrical current generating a heat source.

As particularly represented in FIG. 2, each static freezing valve identified above comprises, for the freezing of the liguid medium of the sample that is treated, and/or any other liguid agent circulating in the treatment circuit 6:

a duct element 29 designed to receive the liquid medium in its passage cross section 29a, the wall of which is thermally conductive, a heat sink 28, represented in outline and in common with FIG. 1, arranged in thermal contact, in particular in heat exchange with the duct element 29, the temperature and the cooling power of which are tailored to the freezing of the liquid medium in the passage cross section 29a the duct element 29 being dimensioned in relation with the heat sink 28 and the heat source generated by passing through it the electrical current output by the electrical source 5, to change rapidly, for example within an elementary time of less than 10 seconds, from a cold state, in which the liquid medium can, by freezing, seal the passage through said duct element, including against relatively high pressures, for example at least equal to 50 bar, in particular 150 bar, to a hot state in which the liquid medium is liquefied, releasing said passage.

In consequence, as emerges from the above description, virtually all the treatment circuit 6, and consequently the active module A, is designed for full internal incineration, simply by passing an electrical current through the constituent materials of said circuit.

The circulation of the liquids in the first chamber 1, or first duct element 3, is controlled by the static freezing valves 16 and 17, respectively at the inlet 1a and at the outlet 1b of the duct element 3. The circulation of the liquids in the second chamber 2 is controlled by the static valves 22 and 23, respectively at the inlet 2a and at the outlet 2b of the second duct element 4.

Three secondary inlets 11 to 13, respectively for three washing liquids 30 to 32, namely, respectively, guanidium thiocyanatee ethanol and acetone, are arranged on the treatment circuit 6, between the outlet 1b of the first chamber and the inlet 2a of the second chamber.

A secondary inlet 33 for an elution liquid 34 is arranged on the treatment circuit, between the outlet 1b of the first chamber and the inlet 2a of the second chamber 2, downstream of the secondary inlets 11 to 13.

The secondary inlets 11 to 13 and 33 are controlled respectively by the valves 18 to 21, and these are static freezing valves.

In the treatment circuit 6, the outlet 2b of the second chamber 2 communicates with a container 35 for collecting the liquid effluents, via a static freezing valve 24.

In the treatment circuit 6, the inlet 1a of the first chamber 1 communicates with a container 36 for an aqueous medium, via a static freezing valve 15. The same container 36 communicates with the collection container 35, via a duct element 10' controlled by the static freezing valve 24.

An intermediate storage vessel 37 is arranged in the treatment circuit 6, between the outlet 2b of the second chamber 2 and the main outlet 8. Two secondary outlets 38 and 39, optionally for liquid and/or gas phase, for depressurizing the treatment circuit 6 and/or flushing this same circuit with a gas, communicate with the circuit 6, downstream of the outlet 2b of the second chamber 2. The secondary outlet 38 is arranged on the container 35 for collecting the effluents, and the secondary outlet 39 is arranged above the intermediate storage vessel 37, while being controlled by a static freezing valve 27.

The container 36 for the aqueous medium, the containers for storing the washing liquids 30 to 32, the container for storing the elution liquid 34, and the container 35 for collecting the liquid effluents are arranged outside the chamber 26 that contains the treatment circuit 6 proper.

For the purpose of analyzing a nucleic fraction or constituent of cells that are contained in a culture sample in the container B, the following operating protocol is employed, using the analysis assembly described above.

For the purpose of the following description, closing or opening a static freezing valve 16 or 17 respectively indicates freezing the liquid medium in its passage cross section, by means of the heat sink 28, and passing an electrical current through the body of the duct element, for the purpose of heating and liquefying this same liquid medium, and thus releasing the passage in said duct element.

Using any suitable means, for example by suction of the liquid sample in the container B, the sample to be treated is transferred to the first chamber 1, the valve 16 being opened and the valve 17, initially open, being closed by freezing on contact with the liquid sample. The interior of the chamber 1 becomes isolated and filled with the sample to be treated, by closing the valve 1b. By passing an electrical current through the first duct element 3, the valves 16 and 17 still being closed, the liquid medium is, on the one hand, vaporized and the pressure of the same medium inside the duct element 3 is raised to relatively high values, on the other hand, so that the cellular material becomes lyzed, releasing the nucleic fraction or fractions to be analyzed, albeit mixed with other residual fractions, in particular proteinic fractions, originating from the same cellular material.

The second chamber is provided with means making it possible to fix or retain the intended nucleic fraction, which are arranged in the second duct element 4 and, for example, consist of an adsorbent material, in particular silica.

By opening the valves 17 and 22, the valve 23 being closed, the lysed sample comprising the nucleic fraction of interest and the residual fractions, is transferred, for example by suction, to the second duct element 2. The nucleic fraction of interest is adsorbed on said adsorbent material of the second chamber 2.

Next, by successively opening the valves 18 to 20 and the valves 22, 23 and 24, for example by suction, the residual fractions of the lysed sample are transferred to the collection container 35, it being understood that the valve 25 is closed.

The second chamber is thus rinsed by the rinsing liquids 30 to 32, respectively, the effluents being discharged to the collection container 35. In this way, the fractions other than nucleic fractions are removed from the second chamber 2.

By closing the valve 24, and by successively opening, the valves 21, 22, 23 and 25, by suction in the vessel 37, the elution liquid 34 is circulated in the second chamber 2, this liquid specifically and solely entraining with it the nucleic fraction when it passes through the second chamber 2, this fraction being in suspension in the intermediate storage vessel 37. The same elution fraction can then be transferred, for example again by suction, to the outer container or card C for analysis, via the main outlet 8. It is actually in this card that, using suitable means which do not form part of the present invention, the analysis proper of the nucleic fraction is carried out, for example by amplification and/or detection, using reagents already available or added in the outer, analysis container C.

The valve 27 being opened by any suitable means, either by suction or by delivery, sterile air is circulated throughout the treatment circuit, and is discharged through the secondary outlets 38 and 39.

Optionally, and if necessary, the elution liquid may be transferred, in the same way and using the same means, through the second chamber 2 and the vessel 37, to the outer analysis container C.

By opening the valves 15 and 24, the valve 25 being closed, and still by suction, all of the treatment circuit 6 is washed using the aqueous medium 36. By means of the secondary outlets 38 and 39, all the valves of the circuit being open, drying air is circulated in said circuit. By passing an electrical current through all of the treatment circuit 6, all the internal surfaces thereof are heated to a temperature that allows full incineration of the organic or biological materials, which leads to complete decontamination of said circuit. The vessel 37 is decontaminated by any suitable thermal means (not shown) After complete decontamination of the treatment assembly, the valve 25 is closed by freezing, by feeding the aqueous medium 36 through the duct element 10.

Lastly, cooling air may be circulated through this same circuit 6, as already done with the drying air. The active module A is then ready for a new analysis, based on a new sample in the container B, and with a new external analysis container C.

We claim:

1. An assembly for treating a sample in a liquid medium, comprising:
   an essentially static, active module being a treatment circuit and being closed off from the outside, the circuit being substantially made from a material capable of dissipating heat by ohmic effect and combining,
   a main inlet for said sample to be treated,
   a first chamber in communication with said main inlet and for dissociating said sample in order to release a predetermined fraction comprising a constituent of interest, the first chamber being a first duct,
   a second chamber for separating said predetermined fraction, the second chamber being a second duct,
   at least one connecting duct between said first and second ducts,
   at least one secondary inlet for at least one of a liquid and a gaseous treatment agent, said at least one secondary inlet connected to said at least one connecting duct,
   a main outlet in communication with said second chamber and for said predetermined fraction,
   at least one electrical source connected to each of said first duct, said second duct and said connecting duct to selectively pass an electrical current through at least one of said first duct, said second duct and said connecting duct to generate heat in at least said selected at least one of said first duct, said second duct and said connecting duct,
   at least one secondary outlet in communication with said second chamber and for effluents, and
   at least one valve between said main inlet and said main outlet;
   a disposable outer container for said sample, said disposable outer container being connectable to said main inlet; and
   a second disposable outer container for analysis, connectable to said main outlet.

2. Assembly according to claim 1, wherein the at least one valve is a static valve involving freezing of the liquid medium of the sample and/or any other liquid agent circulating in the treatment circuit, and the at least one valve comprises a valve duct element designed to receive the liquid medium in its passage cross section, the wall of the valve duct element being thermally conductive, a heat sink is arranged in thermal contact with and in exchange with said valve duct element, the temperature and the cooling power of which are tailored to the freezing of the liquid medium in said passage cross section, said valve duct element being dimensioned, in relation with the heat sink and the heat source generated by passing an electrical current through it, to change within an elementary time of less than ten seconds, from a cold state, in which the liquid medium freezes to seal the passage through said valve duct element, to a hot state in which the liquid medium is liquefied, releasing the passage, wherein in the cold state the passage is sealed against relatively high pressures at least equal to 50 bar.

3. Assembly according to claim 1, the at least one secondary inlet being for a washing liquid located on the treatment circuit, between an outlet of the first chamber and an inlet of the second chamber.

4. Assembly according to claim 1, the at least one secondary inlet being for an elution liquid located on the treatment circuit, between an outlet of the first chamber and an inlet of the second chamber.

5. Assembly according to claim 1, wherein said at least one secondary outlet communicates with a container that is external to said treatment circuit for collecting the liquid effluents.

6. Assembly according to claim 5, further comprising:

at least one additional secondary outlet for gas phase which communicates with the container for collecting the liquid effluents.

7. Assembly according to claim 1, wherein the treatment circuit further comprises an inlet to the first chamber that communicates with a container that is external to said treatment circuit for an aqueous medium.

8. Assembly according to claim 1, further comprising:

a container for an aqueous medium that is connected to the main inlet via a valve in said treatment circuit; and a collection container in communication with said container for an aqueous medium via a duct element in said treatment circuit.

9. Assembly according to claim 1, further comprising:

an intermediate storage vessel located in the treatment circuit, between an outlet of the second chamber and the main outlet.

10. Assembly according to claim 9, further comprising:

at least one additional secondary outlet for gas phase which communicates with the intermediate storage vessel.

11. Assembly according to claim 1, further comprising:

at least one additional secondary outlet for liquid and gas phase for depressurizing the treatment circuit and flushing said circuit with a gas, the at least one additional secondary outlet communicates with said circuit, downstream of an outlet of the second chamber.

12. The assembly of claim 1, the at least one electrical source capable of passing enough electrical current through said first duct, said second duct and said connecting duct to generate enough heat to provide full internal incineration of said circuit.

\* \* \* \* \*